United States Patent [19]

Boyles et al.

[11] 4,411,684

[45] Oct. 25, 1983

[54] AUXIN COMPOSITIONS OF N-PHENYL AND N-CHLORO PHENYL INDOLYL-3-ALKYLENE AMIDES AND THEIR USE AS AUXIN GROWTH REGULATORS

[75] Inventors: David A. Boyles; Jack R. Gaines, both of Rapid City, S. Dak.; Bruce E. Haissig, Rhinelander, Wis.

[73] Assignee: The United States of America as represented by the Secretary of Agriculture, Washington, D.C.

[21] Appl. No.: 367,639

[22] Filed: Apr. 12, 1982

[51] Int. Cl.³ .................. A01N 43/38; C07D 209/18
[52] U.S. Cl. ........................................ 71/77; 548/494
[58] Field of Search ............................ 548/494; 71/77

[56] References Cited
U.S. PATENT DOCUMENTS 4,297,125  10/1981  Haissig et al. .................. 548/494 X Primary Examiner—Nicholas S. Rizzo
Assistant Examiner—D. B. Springer
Attorney, Agent, or Firm—M. Howard Silverstein; David G. McConnell

[57] ABSTRACT

Aryl esters and substituted aryl esters of indole-3-alkanoic acids, such as indole-3-acetic and indole-3-butyric acids, are prepared by a chemical reaction mixture of the acid, a phenol, thiophenol or substituted phenol, a halogenated alkylpyridinium salt, and a tertiary amine in an organic solvent, stirring the mixture for a period of time, and isolating and purifying the product by standard procedures. An aryl amine or substituted aryl amine is substituted for phenol in the reaction mixture when the N-phenyl or N-substituted phenyl indolyl-3-acetamide or butyramide is the desired product. N-phenyl or N-substituted phenyl indolyl-3-acetamides are particularly effective as auxin plant growth regulators and adventitions root initiators.

4 Claims, No Drawings

AUXIN COMPOSITIONS OF N-PHENYL AND N-CHLORO PHENYL INDOLYL-3-ALKYLENE AMIDES AND THEIR USE AS AUXIN GROWTH REGULATORS

FIELD OF THE INVENTION

The invention relates to a novel process for preparing N-phenyl and N-substituted phenyl indolyl-3-acetamides, and N-phenyl and N-substituted phenyl indolyl-3-butyramides and their use as synthetic plant growth hormones.

The invention also relates to a process of producing indole-3-thioloacetate and indole-3-thiolobutyrate and their use as synthetic plant growth hormones.

Similarly, the invention also relates to a process of producing phenyl and substituted phenyl indolyl-3-alkanoic esters.

CROSS-REFERENCE TO RELATED APPLICATIONS

This application is a companion case in relation to our concurrently filed U.S. patent application Ser. No. 367,638, entitled "A Novel Synthesis of Aryl Esters and Thioesters of Indole-3-acetic and Indole-3-butyric acids and their Use as Auxin Growth Regulators", incorporated by reference.

Moreover, the disclosure in the instant application is related to that set forth in the allowed U.S. patent application to Haissig et al., Ser. No. 052,656, filed June 27, 1979 and entitled "Improved Tree Rooting Using Synthetic Auxins", now U.S. Pat. No. 4,297,125, issued Oct. 27, 1981, the disclosure of which is incorporated herein by reference.

BACKGROUND OF THE INVENTION

Naturally occurring auxins, which are plant hormones which in minute quantities act to promote or modify plant growth as in root formation, are known. Such compositions include indole-3-acetic acid (hereinafter denoted IAA) which is known to stimulate adventitious root formation in cuttings of the easy-to-root plants, otherwise known as "good rooters" (Went et al. 1937, Phytohormones, Mac Millan Co., N.Y. page 294). Synthetically prepared auxins such as indole-3-butyric acid (IBA) and Naphthalene-acetic acid (NAA) have more effectively induced rooting in cuttings, particularly cuttings of difficult-to-root species, otherwise known as "poor rooters" (Audus, 1959, Plant Growth Substances, 2nd edition, Interscience Publications Inc., N.Y., page 553; also see Hartmann and Kester, 1975, Plant Propagation, 3rd edition, Prentice-Hall, Inc., Englewood Cliffs, N.J.)

Simple phenols, when administered in admixture with an auxin sometimes cause a synergistic response in adventitious root initiation (Haissig, 1974, Influences of auxins and auxin synergists on adventitious root primordium initiation and development, New Zealand Journal of Forestry Science 4(2); 311–323; also Gorter, Physio. Plant. 1962, 15: 88 to 95). Several theories have been proposed to explain the synergism, one theory being that auxin molecules become bonded to the phenolic moiety and that the conjugated composition induces root initiation more effectively than either the auxin or the phenolic compound individually.

Methyl or ethyl esters of auxins have sometimes been shown to enhance adventitious root initiation more effectively than the corresponding free acids (Veldstra, 1944, Researches on Plant Growth Substances, Enzymologia II, pp. 97–163). The naturally occurring auxin IAA at times appears naturally esterified to form other compounds, and poorly defined auxin phenolic conjugates have been reported (Schantz, 1966, Chemistry of naturally occurring growth regulating substances, Ann. Rev. Plant Physiology, 17:409–438).

A U.S. patent to Grace, U.S. Pat. No. 2,204,213 discloses the use of indole-3-acetic acid, indole-butyric acid, naphthyl acetic acid, phenyl-acetic acid, indole-propionic acid and the salts and esters thereof as auxins or plant hormones for stimulating seed germination and plant growth therefrom of wheat, barley, soya bean and tomato seeds.

Among the known auxins, IAA does not appear to work effectively as a rooting hormone on woody as opposed to herbaceous cuttings. All commercially available rooting hormone preparations comprise IBA, NAA, amides of naphthylene-acetic acid, mixtures of the foregoing, or mixtures of the foregoing with IAA. These synthetic auxin preparations have been available for many years but are generally unsatisfactory as plant hormone root initiators for "poor rooters" and "non-rooters", and prior to Ser. No. 052,656 no more effective preparations have appeared over the years despite the need for more effective plant rooting hormones (New Vistas in Plant Propagation, International Plant Propagators Society Combined Proceedings, 1977, 27:106–113).

It has been reported that phenyl indole-3-acetate (P-IAA) produced 2 to 4 times as many root primordia per leafy bean cutting (Top Crop), an herbaceous plant, (Influence of phenyl indole-3-acetate on adventitious root primordium initiation and development, Plant Physiology (Supplement) 61 (4):65).

A logical applied compound to enhance root primordium initiation (other than mixtures of auxins and phenolics, as described above) would appear to comprise a molecule resulting from a carboxylic acid-phenol esterification reaction, or an analogue or derivative thereof. Synthesis of such esters as phenyl indole-3-butyrate and 3-hydroxyphenyl indole-3-acetate has been attempted (Nekuda, 1976, Synthesis of derivatives of indole-3-acetic acid, M.S. Thesis, South Dakota School of Mines and Technology; Giacoletto, 1978, Synthesis of derivatives of indole-3-acetic acid, M.S. Thesis, South Dakota School of Mines and Technology). The Nekuda and Giacoletto MS theses are both incorporated herein by reference. Testing the aforementioned aryl esters on bean (Phaseolus vulgaris cv. Top Crop) cuttings provided that phenyl and 3-hydroxyphenyl indole-3-acetate are ten or more times as effective, on a molar basis, as compared with indole-3-acetic acid. These esters had no effect on jack pine (Pinus banksiana Lamb.) cuttings because only more active synthetic auxins, such as indole-3-butyric acid (IBA) and naphthalene acetic acid (NAA) usually induce primordium root initiation in woody plant cuttings to any substantial degree (Haissig, 1979, Influence of aryl esters of indole-3-acetic acid and indole-3-butyric acids on adventitious root primordium initiation and development, Physiologia Plantarum 47:29–33).

Phenyl indole-3-butyrate, however, yielded more rooted jack pine cuttings than did indole-3-butyric acid treatment. It was therefore concluded that certain aryl esters may be synthesized that are more effective in inducing adventitious root initiation than other phenyl or 3-hydroxyphenyl esters and than other aryl esters of non-indole auxins, such as naphthalene-acetic acid (Haissig et al. patent application Ser. No. 052,656, referred to above).

The development of new synthetic procedures for preparing new auxins or plant growth regulators is discussed in an article published in 1980; see Boyles M.S. thesis, South Dakota School Mines and Technology. This Boyles M.S. thesis is likewise incorporated herein by reference.

SUMMARY OF THE INVENTION

Priorities in this investigation were directed toward synthesis of analogues of the already successfully synthesized and tested phenyl indole-3-butyrate and phenyl indole-3-acetate. Halogenated aromatics are noted for activity in plants (as herbicides, fruit thinners, ripeners, drop-controllers, etc.) Thus, 4-chloro; 2,4-dichloro and 2,4,6,-tribromo derivatives were pursued.

In prior work leading to the instant invention, Haissig suggested a 3,4-dihydrocinnamic acid/indole-3-acetic acid conjugate. Such an esterification is inherently quite difficult, and work was carried out to protect the acid by esterification with methanol. However, further attempts to esterify one of the remaining two hydroxy groups of caffeic acid were unsuccessful; see Giacoletto M.S. thesis mentioned supra.

The logic behind use of caffeic acid is the evidence supporting its involvement in the shikimic acid pathway which leads along one route to lignin formation. Woody plants, as they mature, become increasingly difficult to root. "Changed phenol metabolism associated with aging or enhanced rates or amounts of lignification might drastically impair the predisposition of cells to initiate root primordia, if it reduces the synthesis of auxin/phenolic conjugates by limiting the supply of suitable phenolics"*. The postulated biogenic sequence leading to lignin formation involves cinnamic→4-coumaric→caffeic-ferulic→sinapic.

*. Hassig, B. E. 1974. Influences of auxins and auxin synergists on adventitious root primordium initiation and development. New Zealand Journal of Forestry Science 4(2):311-323.

The current investigation has made use of acids other than caffeic, yet acids which are also found in the shikimic pathway, viz. 4-coumaric (4-hydroxycinnamic acid); ferulic (4-hydroxy-3-methoxycinnamic acid) and sinapic (3,5-dimethoxy-4-hydroxycinnamic acid), all of which contain only two hydroxy groups as opposed to the three of caffeic acid. In each case we proposed to esterify the acids with methanol. leaving a lone free phenolic hydroxy group for subsequent esterification with indole carboxylic acids.

Haissig had earlier considered a compound for testing derived from a phenolic lying outside the pathway of cinnamic acid metabolism. viz. 4-hydroxybenzoic acid, which itself has been shown to occur naturally as a growth regulator; see Haissig 1974 publication supra. It was therefore proposed to esterify first with ethanol, and then with indole carboxylic acids.

By structural analogy, we proposed amides using aniline and 4-chloroaniline as a substitute for the phenol moiety and thioesters using thiophenol as a substitute for the phenol moiety, in order to assess the electronic and/or size effects of the substituted atoms.

The invention herein concerns a novel chemical procedure for preparing aryl amides of indole-3-acetic acid and indole-3-butyric acid and related esters and thioesters in higher yield and purity than has previously been achieved; and it also concerns novel rooting hormone compositions including such aryl amides.

Therefore, an object of the invention is to use such aryl amides as improved synthetic auxins, or plant hormones, for achieving more effective adventitious root initiation.

It is another object of the invention to overcome the deficiencies in the prior art, which have been extensively discussed above, with a view to more effectively induce rooting in difficult-to-root plant species, including trees.

It is yet another object is to provide a process for making improved synthetic auxins.

These and other objects of the invention are achieved by the synthesis and tested physiological use of N-phenyl and N-substituted phenyl indolyl-3-acetamides and indolyl-3-butyramides and related esters as more potent synthetic auxins for initiating adventitious root primordium development.

DETAILED DESCRIPTION OF PREFERRED EMBODIMENTS

Among the esterification processes mentioned in the Nekuda M.S. paper, supra, were those utilizing mixed anhydrides and acid chlorides, neither of which were acceptable for the esterification of indole alkanoic acids. Nekuda, therefore, investigated the use of dicyclohexylcarbodiimide as a reagent, in such esterification reaction. This reagent is known to be effective in peptide synthesis reaction (Fox et al. 1957, Introduction to Protein Chemistry, John Wiley & Sons, Inc. N.Y. pp. 169-170). Giacoletto (see M.S. paper supra) used dicyclohexylcarbodiimide as a reagent to produce a effective yield (17%) of phenyl indole-3-butyrate. In the dicyclohexylcarbodiimide esterification process it is difficult to separate the fluffy dicyclohexylurea needles, which are produced from the sticky ethereal solution of the ester reaction product. Any solvent used to liberate the ether inherently functions to dissolve the dicyclohexylurea needles, which mandates repetitious crystallizations and filtrations (which normally exceeds five cycles of such procedure). There is no way, known to the prior art, to circumvent these difficulties. In the Giacoletto process, mentioned supra, similar difficulties were encountered in attempting to produce the halogenated derivatives of the phenyl indole esters.

In order to overcome the above problems, new methods have been developed to produce aryl amides of indole-3-acetic and indole-3-butyric acids in purer form and in higher yields than has hitherto been accomplished.

Applicants' novel process for synthesizing amides, esters and thioesters of indolealkanoic acids, as more fully described in the examples set forth below, was developed particularly for attaining the objectives indicated above.

EXAMPLE 1

Initially, 0.0030 moles or 0.610 grams of indole-3-butyric acid, 0.0030 moles or 0.273 ml aniline, 0.003 moles or 0.766 grams of 2-chloro-1-methylpyridinium iodide and 0.0060 moles or 0.837 ml. of triethylamine were added to 25 ml. of methylene chloride in a 50 ml. round-bottom flask fitted with a reflux condenser.

In the instant example, other tertiary amines, such as cross-linked poly-4-vinyl pyridine, can be used instead of triethylamine. Moreover, instead of the 2-chloro-1-methylpyridinium iodide reagent used in the above reaction, other reagents such as 2-bromo-1-ethyl-pyridinium tetrafluoroborate or 2-chloro-1-ethyl-pyridinium iodide can be employed.

Additionally, other solvents having similar physical and chemical characteristics can be substituted for the methylene chloride solvent described in the above reaction.

Reflux of the above dispersed mixture was carried out for about six hours. However, stirring for 24 hours without reflux produced comparable reaction results. The product was separated and purified by standard procedures. The amide reaction product was chemically and physically identified by determining its melting point to be within the range of 69°–72° C. using a Fisher-Johns melting point apparatus and by obtaining infrared spectra using a Beckman, Model IR-10, double beam spectrophotometer. Solid samples of the amide were dispersed in a potassium bromide matrix while liquid samples of the amide were spread on silver chloride places. The scan speed of the spectrophotometer was 14 minutes. Quantitative carbon, hydrogen and nitrogen determinations were made on the amide by Galbraith Laboratories, located in Knoxville, Tenn. The amide reaction product, described above, was chemically identified as N-phenyl indole-3-butyramide and was recovered in a yield calculated to be 92 percent.

EXAMPLE 2

N-phenyl indolyl-3-acetamide was recovered and chemically identified in similar fashion, by following the procedure set forth above in Example 1 except that 0.0030 moles of indole-3-acetic acid was substituted for the indole-3-butyric acid reagent of Example 1.

EXAMPLE 3

N-(4-chlorophenyl) indolyl-3-butyramide was similarly recovered and chemically identified by following the procedure set forth in Example 1 except that 0.0030 mole of 4-chloroaniline was substituted for the aniline reactant of example 1.

EXAMPLE 4

N-(4-chlorophenyl) indolyl-3-acetamide was similarly recovered and chemically identified by following the procedure described in Example 2 except that 0.0030 mole of 4-chloroaniline was substituted for the aniline reactant of Example 2.

EXAMPLE 5

Indolyl-3-thiolacetate was similarly recovered and chemically identified by following the procedure described in Example 2 except that 0.0030 mole thiophenol was substituted for the aniline reactant of Example 2.

A number of substituted phenyl indolyl-3-alkanoic esters were produced by substituting phenols for the anilines used in the above process. Such esters include 2,4-dichlorophenyl indole-3-butyrate; 2,4,6-tribromophenyl indole-3-acetate; 4-carbethoxyphenyl indole-3-acetate; 4-carbethoxyphenyl indole-3-butyrate; 4-(carbomethoxyvinylenephenyl) indole-3-acetate; 4-(carbomethoxyvinylenephenyl) indole-3-butyrate; 4-(carbomethoxyvinylene 2,6-dimethoxyphenyl) indole-3 acetate and 4-(carbomethoxyvinylene-2,6-dimethoxyphenyl) indole-3-butyrate.

The new method described supra is particularly reliable for the synthesis of phenyl esters, thioesters and amides in good yield and high purity. The method is convenient because it can be run either at room temperature or under reflux.

BIOASSAYS OF THE ABOVE TYPE ESTERS AND AMIDES

Biaossay of activity of the above type ester and amide products was done in rooting trials with bean (*Phaseolus vulgaris* cv. Top Crop) or jack pine (*Pinus banksiana* Lamb.) cuttings, or with both, as previously described above (Haissig article published 1979).

Current evidence indicates that auxin growth regulating compounds of the types dealt within this research must be structurally intact at the time that plant tissues are treated but that enzymic hydrolysis occurs in plant tissues. Hydrolysis after entry into cells apparently yields the free active auxin. By extension, these new auxin growth regulators seem to be more effective than the parent compounds because of, for example, greater cellular uptake (Haissig, 1979, supra).

It is sometimes desirable to control tests of new compounds with individual hydrolysis products and their mixtures in order to establish which compounds are responsible for the physiological response, if any. In these trials, the new compound was compared with the parent auxin, and sometimes with the probable products that would result from the new compound by enzymatic hydrolysis.

Tables 1–7, below, show the effects of various N-phenyl indolyl-3-alkanoic esters and amides on adventitious root initiation and elongation in bean or jack pine cuttings.

TABLE 1

Effect of N—phenyl indolyl-3-butyramide on adventitious root initiation and elongation in bean cuttings. Data are means based on 100 values from two replications of the experiment in time. An asterisk in the column below a mean indicates that the mean below which the asterisk appears differed significantly (Pr > .05) from the treatment mean in the row where the asterisk appears. Statistical comparisons are based on a Mann-Whitney U-test.

| Treatment | | Conc. | No. primordia per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 10.3 | | | | | | | | |
| (2) | Aniline | 0.2 | | 9.5 | | | | | | | |
| (3) | Aniline | 2.0 | | | 9.0 | | | | | | |
| (4) | IBA | 0.2 | * | * | * | 15.2 | | | | | |
| (5) | IBA | 2.0 | * | * | * | * | 30.7 | | | | |
| (6) | Aniline + IBA | 0.2 each | * | * | * | | * | 14.6 | | | |
| (7) | Aniline + IBA | 2.0 each | * | * | * | * | | * | 27.9 | | |
| (8) | NP—IBA | 0.2 | * | * | * | * | * | * | * | 19.5 | |
| (9) | NP—IBA | 2.0 | * | * | * | * | * | * | * | * | 34.6 |

TABLE 1-continued

| Treatment | | Conc | No. roots per cuttings by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 12.0 | | | | | | | | |
| (2) | Aniline | 0.2 | * | 7.9 | | | | | | | |
| (3) | Aniline | 2.0 | * | | 7.2 | | | | | | |
| (4) | IBA | 0.2 | | * | * | 14.3 | | | | | |
| (5) | IBA | 2.0 | * | * | * | | 17.4 | | | | |
| (6) | Aniline + IBA | 0.2 each | | * | * | | * | 12.0 | | | |
| (7) | Aniline + IBA | 2.0 each | | * | * | | * | | 13.3 | | |
| (8) | NP—IBA | 0.2 | | * | * | | * | | | 10.9 | |
| (9) | NP—IBA | 2.0 | | * | * | | | | | | 14.4 |

Abbreviations:
IBA — indole-3-butyric acid;
NP—IBA — N—phenyl indolyl-3-butyramide

TABLE 2

Effect of N—phenyl indolyl-3-butyramide on adventitious root initiation and development in 89-day-old jack pine seedling cuttings. Data are means based on 200 values obtained from two replications of the experiment in time. An asterisk in the column below a mean indicates that the mean below which the asterisk appears differed significantly (Pr > .05) from the treatment mean in the row where the asterisk appears. Statistical comparisons are based on a Mann-Whitney U-test. All treatments were affected by the quick basal dip method at a concentration of 25 or 125 mmol/l in absolute ethanol. Data were gathered after cuttings were in the rooting bed for 15 or 30 days.

| Treatment | Conc (mmol/l) | % Rooted Day 15 | % Rooted Day 30 |
|---|---|---|---|
| Control | | 2 | 74 |
| IBA | 25 | 40 | 79 |
| IBA | 125 | 23 | 80 |
| NP—IBA | 25 | 55 | 89 |
| NP—IBA | 125 | 30 | 80 |

| | | | No. roots per cutting by treatment no. | | | | | | | | | |
|---|---|---|---|---|---|---|---|---|---|---|---|---|
| Treatment | | Conc | Day 15 | | | | | Day 30 | | | | |
| No. | Name | (mmol/l) | (1) | (2) | (3) | (4) | (5) | (1) | (2) | (3) | (4) | (5) |
| (1) | Control | | 0.02 | | | | | 2.28 | | | | |
| (2) | IBA | 25 | * | 2.68 | | | | * | 9.25 | | | |
| (3) | IBA | 125 | * | * | 1.22 | | | * | * | 15.63 | | |
| (4) | NP—IBA | 25 | * | * | * | 3.58 | | * | * | * | 11.29 | |
| (5) | NP—IBA | 125 | * | | | * | 1.01 | * | * | | * | 12.64 |

| | | | Length (mm) longest root per cutting by treatment no. | | | | | | | | | |
|---|---|---|---|---|---|---|---|---|---|---|---|---|
| Treatment | | Conc | Day 15 | | | | | Day 30 | | | | |
| No. | Name | (mmol/l) | (1) | (2) | (3) | (4) | (5) | (1) | (2) | (3) | (4) | (5) |
| (1) | Control | | 0.02 | | | | | 20.7 | | | | |
| (2) | IBA | 25 | * | 1.02 | | | | * | 43.0 | | | |
| (3) | IBA | 125 | * | * | 0.34 | | | * | | 42.2 | | |
| (4) | NP—IBA | 25 | * | * | * | 0.97 | | * | * | * | 57.8 | |
| (5) | NP—IBA | 125 | * | | * | | 0.31 | * | | | | 46.8 |

| | | | Weight (g) of basal stem plus roots by treatment no. | | | | | | | | | |
|---|---|---|---|---|---|---|---|---|---|---|---|---|
| Treatment | | Conc | Day 15 | | | | | Day 30 | | | | |
| No. | Name | (mmol/l) | (1) | (2) | (3) | (4) | (5) | (1) | (2) | (3) | (4) | (5) |
| (1) | Control | | 0.104 | | | | | 0.195 | | | | |
| (2) | IBA | 25 | * | 0.184 | | | | * | 0.446 | | | |
| (3) | IBA | 125 | * | * | 0.235 | | | * | * | 0.639 | | |
| (4) | NP—IBA | 25 | * | * | | 0.210 | | * | * | | 0.585 | |
| (5) | NP—IBA | 125 | * | * | * | * | 0.290 | * | * | | * | 0.690 |

Abbreviations:
IBA — indole-3-butyric acid;
NP—IBA — N—phenyl indolyl-3-butyramide

TABLE 3

Effect of indole-3-butyric acid, N—phenyl indolyl-3-butyramide, and phenyl indole-3-butyrate on adventitious root initiation and elongation in 6-day-old. jack pine seedling cuttings after 3 weeks of propagation. Cuttings were treated by touching the cut basal surface to undiluted, powdered, crystalline chemical before being placed in the propagation bed. Data are means based on 20 values from one replication of the experiment in time. An asterisk in the column below a mean indicates that the mean below which the asterisk appears differed significantly (Pr > .05) from the treatment mean in the row where the asterisk appears.

| Treatment | No. roots per cutting by treatment no. | % with 1 cm or more dead |
|---|---|---|

| No. | Name | (1) | (2) | (3) | (4) | % rooted | basal stem |
|---|---|---|---|---|---|---|---|
| (1) | Control | 0.5 | | | | 25 | 0 |
| (2) | IBA | | 1.0 | | | 15 | 85 |
| (3) | NP—IBA | * | * | 4.8 | | 90 | 0 |
| (4) | P—IBA | | * | | 2.7 | 50 | 0 |

| | Treatment | Length (mm) longest root per cutting by treatment no. | | | |
|---|---|---|---|---|---|
| No. | Name | (1) | (2) | (3) | (4) |
| (1) | Control | 0.4 | | | |
| (2) | IBA | | 2.2 | | |
| (3) | NP—IBA | * | * | 5.5 | |

TABLE 3-continued

| | | |
|---|---|---|
| (4) | P—IBA | 3.1 |

Abbreviations:
IBA — indole-3-butyric acid;
NP—IBA — N—phenyl indolyl-3-butyramide;
P—IBA — phenyl indole-3-butyrate

TABLE 4

Effect of 4-carbethoxyphenyl indole-3-butyrate on adventitious root initiation and elongation in bean cuttings. Data are means based on 100 values from two replications of the experiment in time An asterisk in the column below a mean indicates that the mean below which the asterisk appears differed significantly (Pr > .05) from the treatment mean in the row where the asterisk appears. Statistical comparisons are based on a Mann-Whitney U-test.

| Treatment | | Conc | No. primordia per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 11.7 | | | | | | | | |
| (2) | MC | 0.2 | * | 13.8 | | | | | | | |
| (3) | MC | 2.0 | * | | 14.8 | | | | | | |
| (4) | IBA | 0.2 | * | * | * | 19.4 | | | | | |
| (5) | IBA | 2.0 | * | * | * | * | 33.5 | | | | |
| (6) | MC + IBA | 0.2 each | * | * | * | * | * | 20.4 | | | |
| (7) | MC + IBA | 2.0 each | * | * | * | * | * | * | 33.9 | | |
| (8) | CEP—IBA | 0.2 | * | | * | * | * | * | * | 14.9 | |
| (9) | CEP—IBA | 2.0 | * | * | * | * | * | * | * | * | 17.1 |

| Treatment | | Conc | No. roots per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 10.8 | | | | | | | | |
| (2) | MC | 0.2 | | 13.2 | | | | | | | |
| (3) | MC | 2.0 | * | | 15.4 | | | | | | |
| (4) | IBA | 0.2 | * | | | 15.1 | | | | | |
| (5) | IBA | 2.0 | * | | | | 18.2 | | | | |
| (6) | MC + IBA | 0.2 each | * | * | * | * | * | 22.1 | | | |
| (7) | MC + IBA | 2.0 each | * | * | * | * | | | 21.5 | | |
| (8) | CEP—IBA | 0.2 | | | * | * | * | * | * | 11.7 | |
| (9) | CEP—IBA | 2.0 | | | | | | * | * | | 14.6 |

Abbreviations:
MC — methyl coumarate;
IBA — indole-3-butyric acid;
CEP—IBA — 4-carbethoxyphenyl indole-3-butyrate

TABLE 5

Effect of 4-carbethoxyphenyl indole-3-butyrate on adventitious root initiation and development in 91-day-old jack pine seedling cuttings. Data are means based on 180 values obtained from two replications of the experiment in time. An asterisk in the column below a mean indicates that the mean below which the asterisk appears differed significantly (Pr > .05) from the treatment mean in the row where the asterisk appears. Statistical comparisons are based on a Mann-Whitney U-test. All treatments were affected by the quick basal dip method at a concentration of 25 mmol/l in absolute ethanol. Data were gathered after cuttings were in the rooting bed for 30 days.

| Treatment | Conc (mmol/l) | % rooted of 180 cuttings per treatment |
|---|---|---|
| Control | — | 80 |
| MC | 25 | 72 |
| IBA | 25 | 91 |
| MC + IBA | 25 each | 91 |
| CEP—IBA | 25 | 89 |

| Treatment | | Conc | No. roots per cutting by treatment no. | | | | |
|---|---|---|---|---|---|---|---|
| No. | Name | (mmol/l) | (1) | (2) | (3) | (4) | (5) |
| (1) | Control | — | 2.8 | | | | |
| (2) | MC | 25 | | 2.8 | | | |
| (3) | IBA | 25 | * | * | 15.2 | | |
| (4) | MC + IBA | 25 each | * | * | | 18.2 | |
| (5) | CEP—IBA | 25 | * | * | * | * | 9.1 |

| Treatment | | Conc | Length (mm) longest root per cutting by treatment no. | | | | |
|---|---|---|---|---|---|---|---|
| No. | Name | (mmol/l) | (1) | (2) | (3) | (4) | (5) |
| (1) | Control | — | 22.0 | | | | |
| (2) | MC | 25 | | 23.0 | | | |
| (3) | IBA | 25 | * | * | 74.6 | | |
| (4) | MC + IBA | 25 each | * | * | | 68.2 | |
| (5) | CEP—IBA | 25 | * | * | * | | 64.4 |

Abbreviations:
IBA — indole-3-butyric acid;
MC — methyl coumarate;
CEP—IBA — 4-carbethoxyphenyl indole-3-butyrate

TABLE 6

Effect of 2,4-dichlorophenyl indole-3-butyrate on adventitious root initiation and elongation in bean cuttings. Data are means based on 100 values from two replications of the experiment in time. An asterisk in the column below a mean indicates that the mean below which the asterisk appear differed significantly (Pr > .05) from the treatment mean in the row where the asterisk appears. Statistical comparisons are based on a Mann-Whitney U-test.

| Treatment | | Conc | No. primordia per cutting by treatment no. | | | | | | | | |
|---|---|---|---|---|---|---|---|---|---|---|---|
| No. | Name | (μmol/l) | (1) | (2) | (3) | (4) | (5) | (6) | (7) | (8) | (9) |
| (1) | Control | | 10.2 | | | | | | | | |
| (2) | DCP | 0.2 | * | 15.7 | | | | | | | |
| (3) | DCP | 2.0 | * | | 16.5 | | | | | | |
| (4) | IBA | 0.2 | * | | | 17.5 | | | | | |
| (5) | IBA | 2.0 | * | * | * | * | 38.5 | | | | |
| (6) | DCP + IBA | 0.2 each | * | | | | * | 16.6 | | | |
| (7) | DCP + IBA | 2.0 each | * | | | | * | | 17.6 | | |
| (8) | DCP—IBA | 0.2 | * | | | | * | | | 17.2 | |
| (9) | DCP—IBA | 2.0 | * | * | * | * | | * | * | * | 35.1 |

TABLE 6-continued

| Treatment No. | Name | Conc (μmol/l) | (1) | (2) | (3) | (4) | (5) | (6) | (7) | (8) | (9) |
|---|---|---|---|---|---|---|---|---|---|---|---|
| (1) | Control | | 2.3 | | | | | | | | |
| (2) | DCP | 0.2 | | 4.7 | | | | | | | |
| (3) | DCP | 2.0 | | | 4.0 | | | | | | |
| (4) | IBA | 0.2 | * | | | 4.3 | | | | | |
| (5) | IBA | 2.0 | * | * | * | * | 8.0 | | | | |
| (6) | DCP + IBA | 0.2 each | | | | | * | 3.4 | | | |
| (7) | DCP + IBA | 2.0 each | | | | | * | | 3.6 | | |
| (8) | DCP—IBA | 0.2 | | | | | * | | | 3.1 | |
| (9) | DCP—IBA | 2.0 | * | * | * | | * | * | * | * | 6.1 |

Abbreviations:
DCP — 2,4-dichlorophenol;
IBA — indole-3-butyric acid;
DCP—IBA — 2,4-dichlorophenyl indole-3-butyrate

TABLE 7

Effect of 2,4-dichlorophenyl indole-3-butyrate on adventitious root initiation and development in 90-day-old jack pine seedling cuttings. Data are means based on 160 values obtained from two replications of the experiment in time. An asterisk in the column below a mean indicates that the mean below which the asterisk appears differed significantly (Pr > .05) from the treatment mean in the row where the asterisk appears. Statistical comparisons are based on a Mann-Whitney U-test. All treatments were effected by the quick basal dip method at a concentration of 25 mmol/l in absolute ethanol. Data were gathered after cuttings were in the rooting bed for 38 days.

| Treatment | | No. roots per cutting by treatment no. | | | Length (mm) longest root per cutting by treatment no. | | | % Rooted |
|---|---|---|---|---|---|---|---|---|
| No. | Name | (1) | (2) | (3) | (1) | (2) | (3) | |
| (1) | Control | 2.9 | | | 45.3 | | | 72 |
| (2) | IBA | * | 12.8 | | * | 72.7 | | 81 |
| (3) | DCP—IBA | * | | 11.9 | * | | 72.7 | 80 |

Abbreviations:
IBA — indole-3-butyric acid;
DCP—IBA — 2,4-dichlorophenyl indole-3-butyrate The following conclusions may be drawn from an interpretation of the physiological test data set forth above in Tables 1–7:

Tests of N-phenyl indolyl-3-butyramide (NP-IBA) indicate that it induced more primordium initiation in bean cuttings, at the same concentration, than did indole-3-butyric acid (IBA) or equimolar mixtures of IBA and aniline (Table 1). Treatment with aniline did not induce more primordium initiation than the control. Treatment with equimolar mixtures of IBA and aniline yielded numbers of primordia equal to those obtained with IBA treatment at the same concentration, and IBA treatment exceeded the control (Table 1).

Only 2.0 μmol IBA treatment induced greater root elongation than the control (Table 1). IBA and NP-IBA treatments at equal concentrations yielded the same number of elongated roots (Table 1).

Tests of NP-IBA on jack pine cuttings generally indicated that, in comparison with IBA treatment, NP-IBA treatment induced more and earlier rooting at an equal or lesser concentration, as indicated by the following data from Table 2:

(1) percent rooted cuttings—Treatment with 25 mmol/l NP-IBA resulted in more rooted cuttings at both days 15 and 30 than any other treatment, including 5 times the concentration of IBA (Table 2).

(2) No. roots per cutting—Treatment with 25 mmol/l NP-IBA produced more roots per cutting at day 15 than did treatment with either 25 or 125 mmol/l IBA. At day 30, treatment with 25 mmol/l NP-IBA gave significantly better results than treatment with an equal concentration of IBA (Table 2).

(3) Length of the longest root per cutting—At day 15, IBA and NP-IBA treatment yielded the same results at equal concentrations. At day 30, the best results were obtained with 25 mmol/l NP-IBA treatment in comparison with both 25 and 125 mmol/l IBA treatment (Table 2).

(4) Weight of basal stem plus roots—(This test measures both the speed of callus formation at the base of cuttings and root production. Roots develop from callus tissue in jack pine cuttings, which usually means that earlier and greater callus development yields earlier and more abundant root production.) At day 15, 25 or 125 mmol/l IBA treatment gave significantly poorer results than did treatment with the same concentration of NP-IBA. At this time, treatment with 25 mmol/l IBA gave results that were equal to those obtained with 125 mmol/l IBA treatment. At day 30, results obtained with 25 mmol/l NP-IBA treatment exceeded results obtained with 25 mmol/l IBA and equalled results obtained with 125 mmol/l IBA (Table 2).

Root-inducing capabilities and phytotoxicity of IBA and NP-IBA were compared in a separate test with jack pine cuttings (Table 3). The previously tested P-IBA was also included as a reference in this test. Overall, the results indicated that, under the conditions of this test, NP-IBA was more potent than IBA in terms of inducing root initiation and elongation, and less toxic than IBA in that NP-IBA treatment did not kill the base of cuttings (Table 3). NP-IBA treatment also was superior to P-IBA treatment in some aspects of this test. For example, NP-IBA treatment resulted in 40 percent more rooted cuttings. In addition, number of roots per cutting and root length were greater than the control after NP-IBA treatment but equal to control after P-IBA treatment (Table 3). Nevertheless, P-IBA treatment yielded 35 percent more rooted cuttings than did IBA treatment, without mortality to the bases of cuttings (Table 3). Therefore, the physiological actions of NP-IBA and P-IBA treatment were much more alike than they were like the actions generated by IBA treatment.

In tests of 4-carbethoxyphenyl indole-3-butyrate (CEP-IBA) on bean cuttings, all treatments yielded more primordia than the control (Table 4). Treatment with a mixture of IBA and methyl coumarate yielded the same number of primordia as did IBA treatment at the same concentration. More primordia were produced when cuttings were treated with IBA or IBA-methyl coumarate mixtures than with equal concentrations of CEP-IBA (Table 4).

Root elongation was equal to the control only when cuttings were treated with 0.2 μmol/l methyl coumarate or CEP-IBA at both concentrations that were tested (Table 4). Root elongation exceeded the control for all other treatments (Table 4). Root elongation was less, in comparison with IBA or the mixture of IBA and methyl coumarate, when cuttings were treated with an equal concentration of CEP-IBA, except at 2.0 µmol/l treatment with IBA and CEP-IBA were equal (Table 4).

Test with jack pine cuttings indicated that CEP-IBA treatment was about equal to IBA treatment and to treatment with the mixture of methyl coumarate and IBA in terms of percent root of cuttings (Table 5). Each of the latter treatments exceeded the control and methyl coumarate treatments (Table 5). However, CEP-IBA treatment was not as effective as treatment with IBA or the mixture of methyl coumarate and IBA in terms of the number of roots per cutting. However, CEP-IBA treatment exceeded both the control and methyl coumarate treatments in terms of number of roots per cutting (Table 5). In terms of root length, CEP-IBA treatment exceeded the control and methyl coumarate treatments and equalled treatment ith the mixture of methyl coumarate and IBA, but was poorer than IBA treatment (Table 5).

In tests of DCP-IBA on bean cuttings, primordium initiation exceeded the control in all treatments (Table 6). At 0.2 µmol/l, all treatments yielded equal numbers of primordia. However, at 2.0 µmol/l, more primordia were produced by IBA and DCP-IBA treatment than by any other treatment, and IBA and DCP-IBA treatment were equal (Table 6).

Root elongation was superior to the control only after treatment with 0.2 µmol/l IBA in comparison with all other treatments at the same concentration (Table 6). At 2.0 µmol/l, root elongation as a results of IBA treatment exceeded all treatments except DCP-IBA, and treatment with DCP-IBA, and IBA yielded equal results (Table 6).

In tests of DCP-IBA on jack pine cuttings, treatment with IBA or DCP-IBA exceeded the control in terms of percent rooted cuttings and these treatments were about equal (80–81 percent rooted) (Table 7). The treatments produced the same number of roots per cutting and the same root length, and each exceeded the control (Table 7).

The ability of a compound to enhance adventitious root initiation has been a classical test of auxin activity. Two of three compounds that were synthesised for the first time by our method are potent auxin growth regulators, as shown by their stimulation of adventitious root initiation.

Under the conditions of biossay that were used here, 4-carbethoxyphenyl indole-3-butyrate (CEP-IBA) does not appear to be as active as auxin as IBA, although CEP-IBA is an auxin. However, 2,4-dichlorophenyl indole-3-butyrate (DCP-IBA) and N-phenyl indolyl-3-butyramide (NP-IBA) are potent auxins, and structurally unique.

In tests with bean and jack pine cuttings, DCP-IBA was equally potent to IBA.

Tests of N-phenyl indolyl-3-butyramide (NP-IBA) with bean and jack pine cuttings indicated that it is a more potent auxin than IBA.

Of the heretofore known indole auxins, IBA has been very potent, particularly for induction of adventitious root initiation in both herbaceous and woody plants. The activity of IBA has now been exceeded twice, by previously reported phenyl indole-3-butyrate and by the new compound N-phenyl indole-3-butyramide, which has been synthesized by our new method and for the first time.

Other compounds of the above type that were synthesized with the new method are presently undergoing physiological testing.

From the foregoing disclosure the following conclusions may be drawn:

1. The sensitive nature of the disclosed compounds and the expense of indolealkanoic reagents have dictated the development of a unique and high-yielding method for the synthesis of new, improved auxins such as by the method disclosed herein, so that the use of the new auxins can become a commercial reality.

2. The new method produces phenyl and substituted phenyl esters and thioesters of indolealkanoic acids in excellent yield and quality 3. The new method produces N-phenyl indolyl-3-butyramide; N-phenyl indolyl-3-acetamide; and N-substituted phenyl amides of indolealkanoic acids in excellent yield and quality.

4. The new method has been used to synthesize structurally unique growth regulators that have proven as effective or more effective than indole-3-butyric acid. These compounds are 2,4-dichlorophenyl indole-3-butyrate; N-phenyl indole-3-butyramide, and indole-3-thiolobutyrate.

5. The new compounds should be particularly useful in inducing adventitious root initiation in plant cuttings, and may prove even more effective with species other than those used for bioassay.

6. Compounds that are structurally similar to those reported here may also be potent auxin growth regulators for use in, for example, inducing rooting of plant cuttings.

The foregoing description of the specific embodiments will so fully reveal the general nature of the invention that others of ordinary skill in the art can by applying current knowledge, readily modify and/or adapt for various applications such specific embodiments without departing from the generic concept, and therefore, such adaptations and modifications should and are intended to be comprehended within the meaning and range of equivalents of the disclosed embodiments. It is understood that the phraseology or terminology employed herein is used for the purpose of description and not of limitation.

What is claimed is:

1. A synthetic auxin composition for stimulating adventitious root formation in difficult-root cuttings, comprising an amount sufficient to simulate adventitious root formation of a compound or mixture of compounds selected from the group consisting of phenyl and chlorophenyl indole-3-lower alkylene amides wherein the alkylene amide group has up to 4 carbons; and a volatile or inert non-toxic carrier.

2. A composition according to claim 1, wherein said compound or mixture of compounds is selected from the group consisting of N-phenyl indole-3-acetamide; N-phenyl indole-3-butyramide; N-(4-chlorophenyl) indole-3-butyramide and N-(4-chlorophenyl) indole-3-acetamide.

3. A composition according to claim 1, wherein said compound is N-phenyl indole-3-butyramide.

4. A method of stimulating adventitious root formation of plant cuttings comprising
contacting the stem of a plant cutting with a phenyl indole-3-lower alkylene amide wherein the amide group has up to 4 carbon atoms, or a mixture thereof; and
maintaining said cutting in an environment for developing roots on the stem of said cutting until the roots develop to an extent that said cutting is suitable for transplanting.

* * * * *